(12) United States Patent
Shkolnikov et al.

(10) Patent No.: US 11,141,729 B2
(45) Date of Patent: Oct. 12, 2021

(54) OBJECT FOCUSING

(71) Applicant: HEWLETT-PACKARD DEVELOPMENT COMPANY, L.P., Spring, TX (US)

(72) Inventors: Viktor Shkolnikov, Palo Alto, CA (US); Alexander N. Govyadinov, Corvallis, OR (US); Pavel Kornilovich, Corvallis, OR (US)

(73) Assignee: Hewlett-Packard Development Company, L.P., Spring, TX (US)

(*) Notice: Subject to any disclaimer, the term of this patent is extended or adjusted under 35 U.S.C. 154(b) by 0 days.

(21) Appl. No.: 16/605,162

(22) PCT Filed: Jan. 24, 2018

(86) PCT No.: PCT/US2018/014965
§ 371 (c)(1),
(2) Date: Oct. 14, 2019

(87) PCT Pub. No.: WO2019/147228
PCT Pub. Date: Aug. 1, 2019

(65) Prior Publication Data
US 2021/0138467 A1  May 13, 2021

(51) Int. Cl.
*B01L 3/00* (2006.01)
*F04B 19/00* (2006.01)

(52) U.S. Cl.
CPC ...... *B01L 3/502776* (2013.01); *F04B 19/006* (2013.01); *B01L 2200/0636* (2013.01); *B01L 2400/0487* (2013.01)

(58) Field of Classification Search
CPC ..... B01L 2200/0636; B01L 2400/0487; B01L 3/502776; F04B 19/006
See application file for complete search history.

(56) References Cited

U.S. PATENT DOCUMENTS 6,708,561 B2  3/2004  Zurek et al.
7,157,274 B2  1/2007  Bohm et al.
(Continued)

FOREIGN PATENT DOCUMENTS

| JP | 2003220322 A | 8/2003 |
| WO | WO2011097032 A1 | 8/2011 |
| WO | WO2017127119 A1 | 7/2017 |

OTHER PUBLICATIONS

Hebert et al. "Dynamic Radial Positioning of a Hydrodynamically Focused Particle Stream Enabled by a Three-Dimensional Microfluidic Nozzle" 2015, Biomicrofluidics, 9(2).

*Primary Examiner* — Jennifer Wecker
*Assistant Examiner* — Jonathan Bortoli
(74) *Attorney, Agent, or Firm* — Tong Rea Bentley & Kim LLC

(57) ABSTRACT

An object focuser may include a substrate, a sample fluid passage supported by the substrate, a first inertial pump supported by the substrate to pump a sample fluid entraining an object through the sample fluid passage, a first sheath fluid passage, a second inertial pump supported by the substrate to pump a first sheath fluid through the first sheath fluid passage, a second sheath fluid passage and a second inertial pump supported by the substrate to pump a second sheath fluid through the second sheath fluid passage. The first sheath fluid passage and the second sheath fluid passage are connected to the sample fluid passage at a convergence on opposite sides of the sample fluid passage.

13 Claims, 4 Drawing Sheets

(56) References Cited

U.S. PATENT DOCUMENTS

| | | | |
|---|---|---|---|
| 7,226,562 B2* | 6/2007 | Holl | B01F 5/0646 |
| | | | 422/50 |
| 8,807,879 B2 | 8/2014 | Toner et al. | |
| 9,381,739 B2 | 7/2016 | Govyadinov et al. | |
| 2005/0092681 A1 | 5/2005 | Higashino et al. | |
| 2009/0211657 A1 | 8/2009 | Dirac | |
| 2012/0307244 A1* | 12/2012 | Sharpe | G01N 15/1484 |
| | | | 356/338 |
| 2016/0341337 A1 | 11/2016 | Govyadinov et al. | |
| 2017/0211741 A1 | 7/2017 | Smith | |

* cited by examiner

OBJECT FOCUSING

BACKGROUND

The focusing and separation of objects such as cells, particles, bubbles and immiscible droplets, is performed in various industries. For example, in biology and medicine, rare cells are often separated from a patient's blood for diagnosis. The focusing and separation of objects, such as rare blood cells, presents many challenges.

Figure 1:
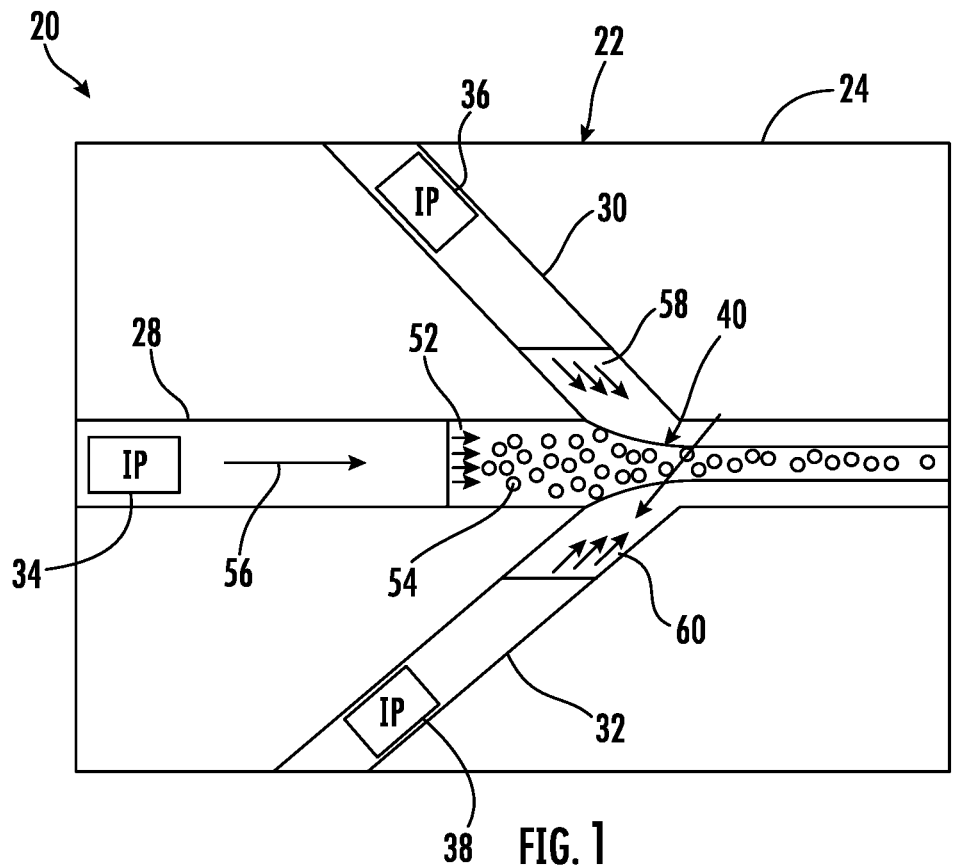
FIG. 1 is a schematic diagram illustrating portions of an example microfluidic device and portions of an example object focuser.

Throughout the drawings, identical reference numbers designate similar, but not necessarily identical, elements. The figures are not necessarily to scale, and the size of some parts may be exaggerated to more clearly illustrate the example shown. Moreover, the drawings provide examples and/or implementations consistent with the description; however, the description is not limited to the examples and/or implementations provided in the drawings.

DETAILED DESCRIPTION OF EXAMPLES

Disclosed herein are example object focusers and object focusing methods that may be used to facilitate the separation of fluid entrained objects out of a volume of fluid. The disclosed object focusers create object entraining flows and sheath flows using inertial pumps. The inertial pumps facilitate low cost and less complex object focusers such that the object focusers may be incorporated onto or as part of microfluidic chips as self-contained object focusing microfluidic chips.

Disclosed herein are example object focusers and object focusing methods that facilitate use of inertial pumps as part of object focuses by reducing an impact of pulsations or waves that may occur as a result of using inertial pumps and that may impair the focusing of the objects in the fluid stream. In one implementation, the example object focusers and object focusing methods reduce the impact of pulsations or waves by coordinating activation of different inertial pumps of a sample fluid passage and sheath fluid passages such that the wave fronts are synchronized or substantially synchronized at a convergence of such passages. In one implementation, "substantial synchronization" occurs such that the beat frequency is less than 1/(time scale of particle separation or processing time). For example if the processing time is 60 s, the beat frequency should be less than 0.02 Hz.

In another implementation, the example object focusers and object focusing methods reduce the impact of pulsations or waves through the use of pulsation dampening chambers that absorb and dissipate the force of such pulsations or waves. In one implementation, the pulsation dampening chambers each have a width at least three times a maximum dimension of an inlet connecting the particular passage to the pulsation dampening chamber and a length at least three times a maximum dimension of the inlet. In another implementation, the pulsation dampening chambers each have a changeable volume to absorb forces of the pulses or waves. For example, in one implementation, each pulsation dampening chamber may have a volume that may be expand by at least 10 pico liters. In one implementation, each pulsation dampening chamber comprises a flexible or stretchable wall or a compressible wall that changes dimensions in response to fluid pressure pulses or waves. In one implementation, each pulsation dampening chamber comprises at least one port forming a gas-liquid interface for forming an expandable meniscus, wherein the meniscus expands contracts to dissipate or absorb fluid pressure pulses or waves.

In some implementations, the object focusers include microfluidic passages or channels. Microfluidic channels may be formed by performing etching, microfabrication (e.g., photolithography), micromachining processes, or any combination thereof in a substrate of the fluidic die. Some example substrates may include silicon based substrates, glass based substrates, gallium arsenide based substrates, plastic based substrates, cellulose or paper based substrates, and/or other such suitable types of substrates for microfabricated devices and structures. Accordingly, microfluidic channels, passages, chambers, orifices, and/or other such features may be defined by surfaces fabricated in the substrate of a fluidic die. Furthermore, as used herein a microfluidic channel or passage may correspond to a channel of sufficiently small size (e.g., of nanometer sized scale, micrometer sized scale, millimeter sized scale, etc.) to facilitate conveyance of small volumes of fluid (e.g., picoliter scale, nanoliter scale, microliter scale, milliliter scale, etc.).

As used herein, an inertial pump corresponds to a fluid actuator and related components disposed in an asymmetric position in a fluid channel, where an asymmetric position of the fluid actuator corresponds to the fluid actuator being positioned less distance from a first end of the fluid channel as compared to a distance to a second end of the fluid channel. Accordingly, in some examples, a fluid actuator of an inertial pump is not positioned at a mid-point of a fluid channel. The asymmetric positioning of the fluid actuator in the fluid channel facilitates an asymmetric response in fluid proximate the fluid actuator that results in fluid displacement when the fluid actuator is actuated. Repeated actuation of the fluid actuator causes a pulse-like flow of fluid through the fluid channel.

In some examples, an inertial pump includes at least one thermal actuator having a heating element (e.g., a thermal resistor) that may be heated to cause a bubble to form in a fluid proximate the heating element. In such examples, a surface of a heating element (having a surface area) may be proximate to a surface of a fluid channel in which the heating element is disposed such that fluid in the fluid channel may thermally interact with the heating element. In some examples, the heating element may comprise a thermal resistor with at least one passivation layer disposed on a heating surface such that fluid to be heated may contact a topmost surface of the at least one passivation layer. Formation and subsequent collapse of such bubble may generate flow of the fluid. As will be appreciated, asymmetries of the expansion-collapse cycle for a bubble may generate such flow for fluid pumping, where such pumping may be referred to as "inertial pumping."

In other examples, the fluid actuator(s) forming an inertial pump may comprise piezo-membrane based actuators, electrostatic membrane actuators, mechanical/impact driven membrane actuators, magnetostrictive drive actuators, electrochemical actuators, external laser actuators (that form a bubble through boiling with a laser beam), other such microdevices, or any combination thereof. In some implementations, the fluid actuators may displace fluid through movement of a membrane (such as a piezo-electric membrane) that generates compressive and tensile fluid displacements to thereby cause inertial fluid flow.

As will be appreciated, the fluid actuator forming the inertial pump may be connected to a controller, and electrical actuation of the fluid actuator by the controller may thereby control pumping of fluid. Actuation of the fluid actuator may be of relatively short duration. In some examples, the fluid actuator may be pulsed at a particular frequency for a particular duration. In some examples, actuation of the fluid actuator may be 1 microsecond (ps) or less. In some examples, actuation of the fluid actuator may be within a range of approximately 0.1 microsecond (μs) to approximately 10 milliseconds (ms). In some examples described herein, actuation of the fluid actuator includes electrical actuation. In such examples, a controller may be electrically connected to a fluid actuator such that an electrical signal may be transmitted by the controller to the fluid actuator to thereby actuate the fluid actuator. Each fluid actuator of an example microfluidic device may be actuated according to actuation characteristics. Examples of actuation characteristics include, for example, frequency of actuation, duration of actuation, number of pulses per actuation, intensity or amplitude of actuation, phase offset of actuation.

Disclosed herein is an object focuser that may include a substrate, a sample fluid passage supported by the substrate, a first inertial pump supported by the substrate to pump a sample fluid entraining an object through the sample fluid passage, a first sheath fluid passage, a second inertial pump supported by the substrate to pump a first sheath fluid through the first sheath fluid passage, a second sheath fluid passage and a second inertial pump supported by the substrate to pump a second sheath fluid through the second sheath fluid passage. The first sheath fluid passage and the second sheath fluid passage are connected to the sample fluid passage at a convergence on opposite sides of the sample fluid passage.

Disclosed herein is an object focusing method that may include pumping a sample fluid entraining an object through a sample passage on a substrate with a first inertial pump on the substrate, pumping a first sheath fluid through a first sheath fluid passage on the substrate with a second inertial pump on the substrate and pumping a second sheath fluid through a second sheath fluid passage on the substrate the third inertial pump on the substrate. The second sheath fluid passage may be connected to the sample passage on a first side of the sample passage at a convergence. The second sheath fluid passage may be connected to sample passage on a second side of the sample passage at the convergence.

Disclosed herein is an example method that may include pumping pulses of a sample fluid entraining an object through a sample fluid passage, pumping pulses of a first sheath fluid through a first sheath fluid passage connected to sample fluid passage at a convergence, pumping pulses of a second sheath fluid through a second sheath fluid passage connected to the sample fluid passage at the convergence and controlling the pumping of the sample fluid, the pumping of the first sheath fluid in the pumping of the second sheath fluid such that the wave fronts of the respective pulses are synchronized at the convergence.

FIG. 1 schematically illustrates portions of an example microfluidic device 20 having an example object focuser 22. Object focuser 22 creates object entraining flows and sheath flows using inertial pumps position on a single substrate of microfluidic chip. The inertial pumps facilitate low cost and less complex object focusers such that the object focusers may be incorporated onto or as part of microfluidic chips. Object focuser 22 comprises substrate 24, sample fluid passage 28, sheath fluid passage 30, sheath fluid passage 32, inertial pumps 34, 36 and 38.

Substrate 24 comprises at least one layer of material or materials. Examples of materials from which substrate 24 may be formed include, not limited to, silicon, glass, ceramics and/or polymers. In one implementation, substrate 24 may be formed from SU8. In other implementations, substrate 24 may be formed from other materials or combinations of materials.

Substrate 24 comprises a series of connected in branching channels formed therein which partially form passages 28, 30 and 32. In one implementation, the different channels comprise internal tubes or passages completely surrounded by the material or materials of substrate 24 (where FIG. 1 is illustrating substrate 24 in section to schematically illustrate the channels/passages). In one implementation, the channels are formed by imprinting or molding of a layer material forming substrate 24. In another implementation, the channels are formed by cutting, ablation, etching or other material removal processes carried out on the layer or layers of material forming substrate 24. In another implementation, the channels are formed by selective deposition, such as printing or additive manufacturing processes carried out upon an underlying base layer or platform.

Fluid sample passage 28 comprises one of the channels formed in substrate 24. Fluid sample passage 28 is connected to a source of fluid containing an object or objects to be subsequently focused and/or separated by focuser 22. Examples of the objects that may be focused and/or separated include, but are not limited to cells, particles, bubbles and immiscible droplets. In one implementation, the objects that may be focused and/are separated consist of objects selected from a group of objects consisting of at least one of cells, particles, bubbles and immiscible droplets. Examples of the fluid used to entrain the objects include, but are not limited to, water, phosphate buffered saline, phosphate buffered sucrose, fluorescence activated cell sorter (FACS) buffer, cell lysate media, cell culture media, blood, blood plasma, blood serum, urine, cerebral spinal fluid, tears and milk. Fluid sample passage 28 guides a flow of the fluid entraining the objects to a convergence 40 with sheath fluid passages 30, 32.

Sheath fluid passages 30 and 32 comprise other channels formed in substrate 24 which connect to sample fluid passage 28 at the convergence 40. Each sheath fluid passage 30, 32 is connected to a source of a sheath fluid, a buffer fluid. In one implementation, the sheath fluid omits any of the particular objects to be focused or separated. Examples of different sheath fluid used include, but are not limited to, water, phosphate buffered saline, phosphate buffered sucrose, FACS buffer, cell lysate media, cell culture media.

Although object focuser 22 is illustrated as comprising two sheath fluid passages 30, 32 on opposite sides of sample fluid passage 28, in other implementations, object focuser 22 may comprise additional sheath fluid passage is distributed about sample fluid passage 28 and also joined a sample fluid passage 28 at convergence 40. Although sheath fluid passages 30, 32 are illustrated as being of the same size and shape as one another and as extending at substantially the same angle as one another, in other implementations, sheath fluid passages 30, 32 may have different sizes (different cross-sectional flow areas), different shapes and may extend at different angles relative to sample fluid passage 28. In some implementations, one or both of sheath fluid passages 30, 32 may have varying shapes or interior damages along the respective lengths.

Inertial pumps 34, 36 and 38 displace fluid and pump fluid along each of their respective passages 28, 30 and 32. Inertial pumps 34, 36 and 38 each comprise at least one fluid actuator formed upon substrate 24 and asymmetrically positioned in respective fluid passages 28, 30 and 32, where an asymmetric position of the at least one fluid actuator corresponds to the fluid actuator being positioned less distance from a first end the respective passage as compared to convergence 40. The at least one fluid actuator forming the inertial pump is not positioned at a mid-point of the passage between the source of the particular fluid and convergence 40. The asymmetric positioning of the at least one fluid actuator in the respective passage facilitates an asymmetric response in fluid proximate the fluid actuator that results in fluid displacement when the fluid actuator is actuated. Repeated actuation of the at least one fluid actuator causes a pulse-like flow of fluid through respective passage towards and to convergence 40.

In some examples, an inertial pump includes at least one thermal actuator having a heating element (e.g., a thermal resistor) that may be heated to cause a bubble to form in a fluid proximate the heating element. In such examples, a surface of a heating element (having a surface area) may be proximate to a surface of respective passages 28, 30, 32 in which the heating element is disposed such that fluid in the microfluidic channel may thermally interact with the heating element. In some examples, the heating element may comprise a thermal resistor with at least one passivation layer disposed on a heating surface such that fluid to be heated may contact a topmost surface of the at least one passivation layer. Formation and subsequent collapse of such bubble may generate inertial flow of the fluid. As will be appreciated, asymmetries of the expansion-collapse cycle for a bubble may generate such flow for fluid pumping, where such pumping may be referred to as "inertial pumping."

In other implementations, the fluid actuators forming the inertial pumps 34, 36 and 38 may comprise piezo-membrane based actuators, electrostatic membrane actuators, mechanical/impact driven membrane actuators, magnetostrictive drive actuators, electrochemical actuators, laser heating, other such microdevices, or any combination thereof. In some implementations, the fluid actuator forming the inertial pumps 34, 36 and 38 may displace fluid through movement of a membrane (such as a piezo-electric membrane) that generates compressive and tensile fluid displacements to thereby cause fluid flow. Each of such inertial pumps 34, 36 and 38 is activated and controlled by electrical signals transmitted from a controller supported by substrate 24 or a remote controller across electric conductive wires, lines or traces formed within or upon substrate 24.

As further shown by FIG. 1, inertial pump 34 inertially pumps sample fluid 52 entraining objects 54 in a direction indicated by arrow 56 towards convergence 40. Inertial pumps 36 and 38 inertially pump sheath fluids 58, 60 towards convergence 40. The streams of sheath fluids 58 and 60 squeeze and focus the fluid and trained objects 54 into a single file or near-single file order or arrangement flowing downstream for further separation, counting or processing. In one implementation, the sheath fluid 1560 may be similar to one another. In another implementation, the sheath fluids 58 and 60 may be different from one another.

Figure 2:
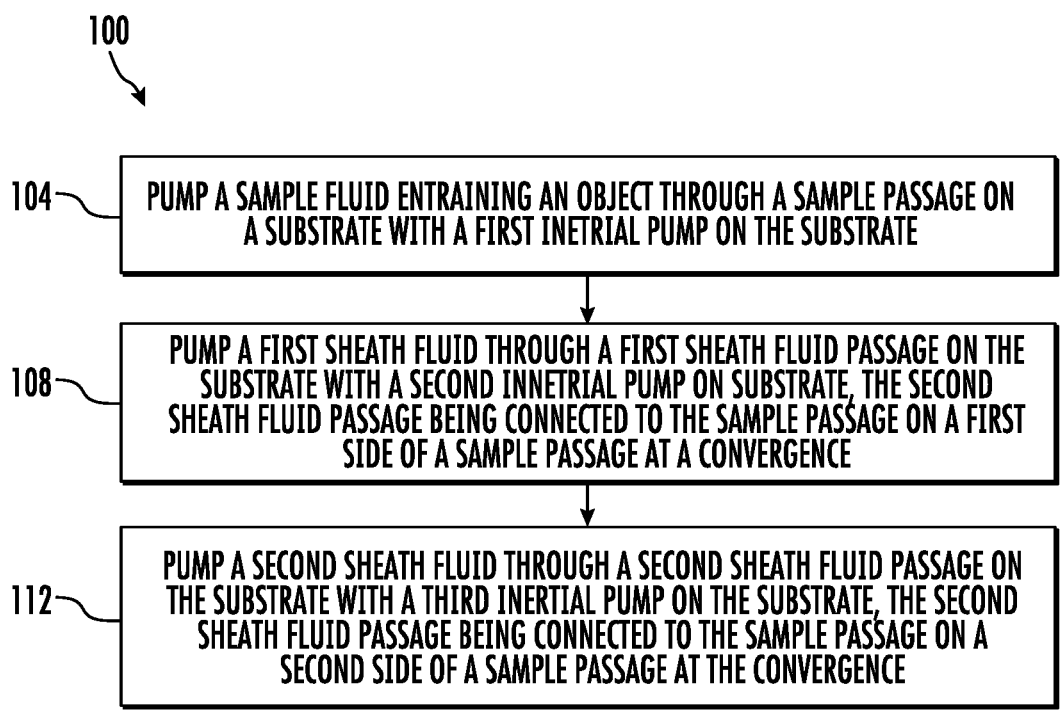
FIG. 2 is a flow diagram of an example object focusing method.

FIG. 2 is a flow diagram of an example object focusing method 100. Object focusing method 100 focuses objects, such as into a single file or near-single file order, using inertial pumps that pump a sample fluid passage and sheath fluid passages. As a result, the method facilitates low cost and less complex object focusing that may be provided on or as part of self-contained object focusing microfluidic chip. Although method 100 is described in the context of being carried out by object focuser 22 of microfluidic device 20 described above, should be appreciated that method 100 may be carried out with any of the object find described hereafter or similar object focusers.

As indicated by block 104, inertial pump 34 pumps a sample fluid 52 entraining at least one object 54 through a sample passage 28 on a substrate 24. As indicated by block 108, inertial pump 36 pumps a first sheath fluid 58 through a first sheath fluid passage 30 on substrate 24. The second sheath fluid passage 30 is connected to sample fluid passage 28 on a first side of the sample fluid passage 28 at a convergence 40. As indicated by block 112, inertial pump 38 pumps a second sheath fluid 60 through a second sheath fluid passage 32 on substrate 24. The second sheath fluid passage 32 is connected to the sample fluid passage 28 on a second side of the sample fluid passage 28 at the convergence 40.

Figure 3:
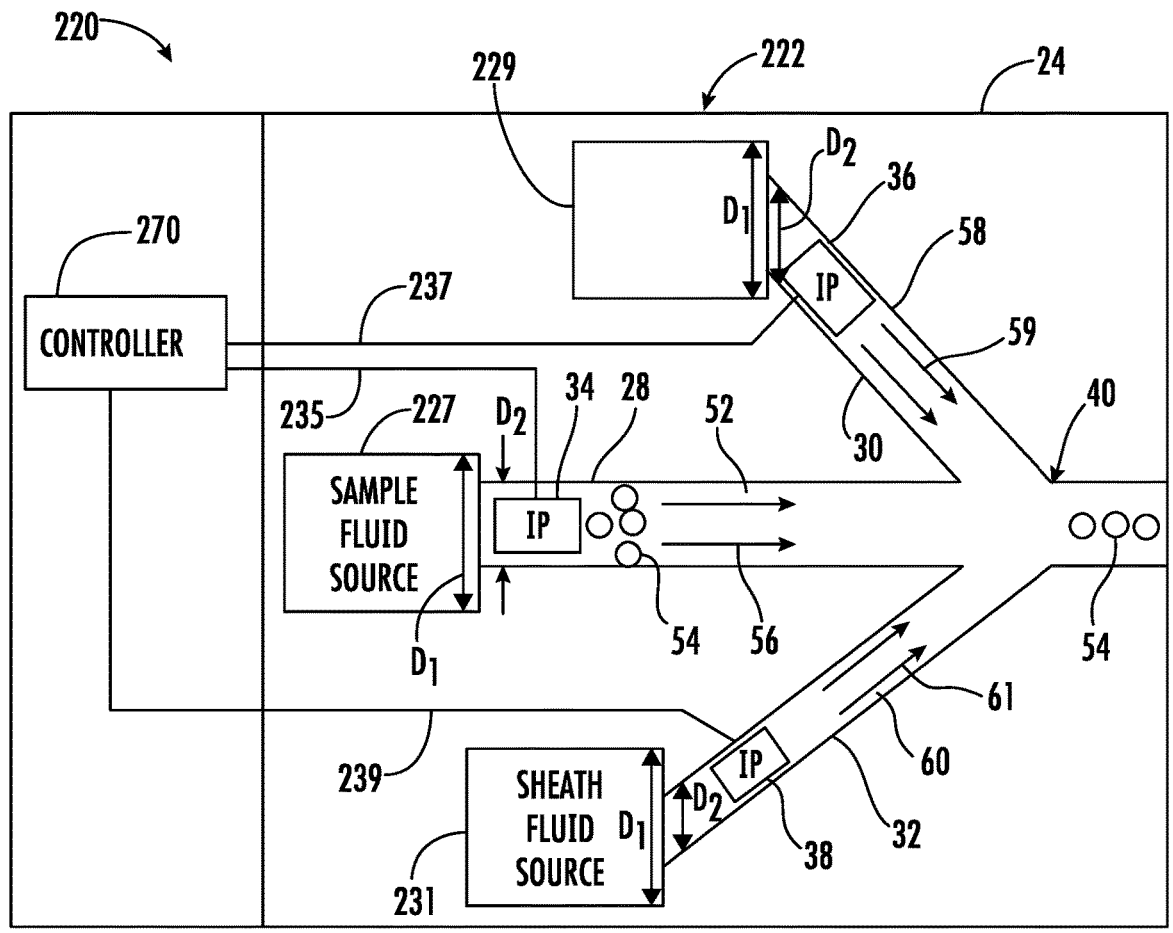
FIG. 3 is a schematic diagram illustrate portions of an example microfluidic device and portions of an example object focuser.

FIG. 3 schematically illustrates portions of an example microfluidic device 220 with portions of an example object focuser 222. Object focuser 222 is similar to object focuser 22 except that object focuser 222 is specifically illustrated as comprising sample fluid source 227, sheath fluid source 229, sheath fluid source 231 and controller 270. Those remaining components of object focuser 222 which correspond to object focuser 22 are numbered similarly.

Sample fluid source 227 comprises a source of the sample fluid 52 entraining objects 54 that is connected to sample fluid passage 28. In one implementation, sample fluid source 227 comprises a reservoir formed in substrate 24 for storing and supplying sample fluid 52. In another implementation, sample fluid source 227 comprises a port through which sample fluid 52 may be provided to microfluidic device 220. Sample fluid source 227 has a fluid containing volume with a dimension D1 at least three times greater than the dimension D2 of sample fluid passage 28 to facilitate inertial pumping in the direction indicated by arrows 56 towards convergence 40. As shown by FIG. 3, inertial pump 34 is asymmetrically positioned within sample fluid passage 28, positioned closer to sample fluid source 227 as compared to convergence 40.

Sheath fluid sources 229 and 231 comprise sources of sheath fluid 58 and 60 that are connected to sheath fluid passage 30 and 32, respectively. In one implementation, sheath fluid sources 229, 231 comprise reservoirs formed in substrate 24 for storing and supplying sheath fluids 58 and 60, respectively. In another implementation, sheath fluid sources 229, 231 comprise ports through which sheath fluid 58 and 60 may be provided to microfluidic device 220. As with sample fluid source 227, each of sheath fluid sources 231 has a fluid containing volume with a dimension D1 at least three times greater than the dimension D2 of the adjacent sheath fluid passage 30, 32 to facilitate inertial pumping of sheath fluid 58 and 60 in the direction indicated by arrows 59 and 61 towards convergence 40. As further shown by FIG. 3, inertial pumps 36 and 38 are asymmetrically position within their respective sheath fluid passages 30 and 32 with inertial pump 36 being closer to sheath fluid source 229 the convergence 40 and with inertial pump 38 being positioned closer to sheath fluid source 231 then convergence 40.

Controller 270 comprises computer or electronic hardware that controls the activation of inertial pumps 34, 36 and 38. In one implementation, controller 270 comprises an integrated circuit, such as an application-specific integrated circuit. In yet another implementation, controller 270 comprises a processing unit that follows instructions, programming or code stored in a non-transitory computer-readable medium. Controller 270 transmits control signals, which control the activation of inertial pumps 34, 36 and 38, across electrically conductive wires or traces 235, 237 and 239, respectively, formed upon or supported by substrate 24. In one implementation, controller 270 is remote or separate from substrate 24, wherein substrate 24 comprises electrical contact pads, plugs or ports for electrically connecting controller 270 to traces 235, 237, 239. In yet another implementation, as shown by broken lines, controller 270 may be formed directly upon substrate 24.

Controller 270 coordinates activation of inertial pumps 34, 36 and 38 to enhance the focusing of objects 54 at convergence 40. In one implementation, controller 270 controls the activation of inertial pumps 34, 36 and 38 such that wave fronts experienced by the pulsing fluid flows through passages 28, 30 and 32 (due to the inertial pumping) are synchronized at convergence 40, forming a single wave front rather than multiple spaced or offset wave fronts which

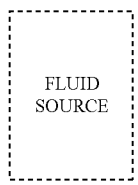

might otherwise detrimentally impact the focusing of objects 54 at convergence 40. As a result, object focuser 222 more effectively focuses objects 54 for subsequent separation, counting or other analysis.

The synchronization of the wave fronts from the different inertial pumps 34, 36 and 38 at convergence 40 may be achieved by controlling the timing at which the different inertial pumps are activated. The timing may depend upon the characteristics of each inertial pump, the dimensions and length of each of the passages 28, 30 and 32, the characteristics of the fluid being pumped as well positioning of the inertial pumps relative to their respective fluid sources and convergence 40. In one implementation in which each of the inertial pumps 34, 36 and 38 are similar to one another, are equally spaced from convergence 40 and the respective fluid sources, and where the fluids being pumped have similar viscosity characteristics, controller 270 may synchronize the activation of the different inertial pumps such that the wave fronts are also synchronized at convergence 40. In other implementations, controller 270 may differently activate the different inertial pumps 34, 36 and 38 (a different frequency of actuation, duration of actuation, number of pulses per actuation, intensity or amplitude of actuation, and/or phase offset of actuation) due to differences amongst at least one of the above factors so as to achieve synchronize wave fronts at convergence 40.

Figure 4:
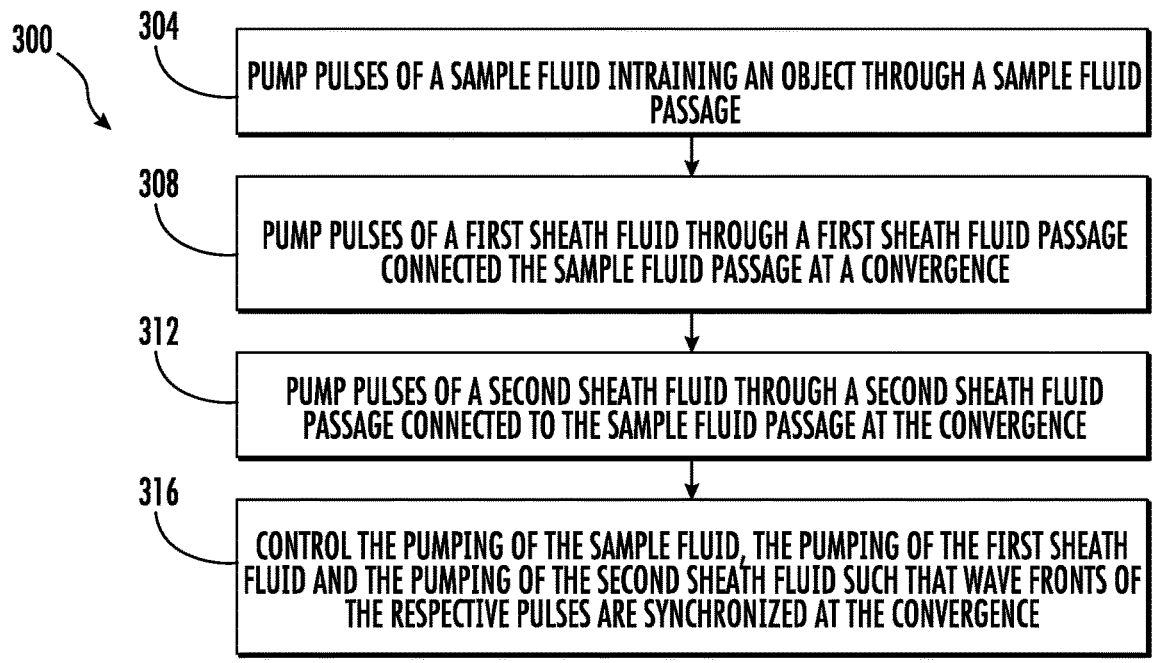
FIG. 4 is a flow diagram of an example object focusing method.

FIG. 4 is a flow diagram of an example object focusing method 300. Object focusing method 300 facilitates the focusing of object using inertial pumps while reducing or mitigating the effects of the pulsing of the inertial pumps to enhance the focusing of objects. Although method 300 is described in the context of being carried out by object focuser 222, it should be appreciated that method 300 may be carried out with any of the object focuser described or other similar object focusers.

As indicated by block 304, pulses of a sample fluid entraining an object are pumped through a sample fluid passage. In one example using object focuser 222, pump 34 inertially pumps pulses of a sample fluid 52 entraining objects 54 through sample fluid passage 28 towards convergence 40. As discussed above, the object 54 may comprise a cell, particle, bubble or immiscible droplet. In one particular implementation, object 54 comprises a cell. In another particular implementation, object 54 comprises a particle. In yet another implementation, object 54 comprises a bubble. In still another implementation, object four comprises an immiscible droplet.

As indicated by block 308, pulses of a first sheath fluid are pumped through a first sheath fluid passage, wherein the first sheath fluid passage is connected to the sample fluid passage at a convergence. In one example using object focuser 222, pump 36 inertially pumps pulses of a sheath fluid 58 through sheath fluid passage 30 towards convergence 40. As indicated by block 312, pulses of a second sheath fluid are pumped through a second sheath fluid passage, wherein the second sheath fluid passage is connected to the sample fluid passage at the convergence. In the example using object focuser 222, pump 38 inertially pumps pulses of a sheath fluid 60 through sheath fluid passage 32 towards convergence 40.

As indicated by block 316, the pumping of the sample fluid, the pumping of the first sheath fluid in the pumping of the second sheath fluid are controlled such that wave fronts of the respective pulses are synchronized at the convergence. In one example using object focuser 222, controller 270 coordinates and controls the separate activations of inertial pumps 34, 36 and 38 such that the wave fronts of the different pulses are synchronized, become substantially one, at convergence 40. The reduction or elimination of the differences between the offset or timing of the different wave fronts of the different pulses enhances focusing of objects 54 into a single file or focused arrangement for more effective separation, counting or other analysis.

Figure 5:
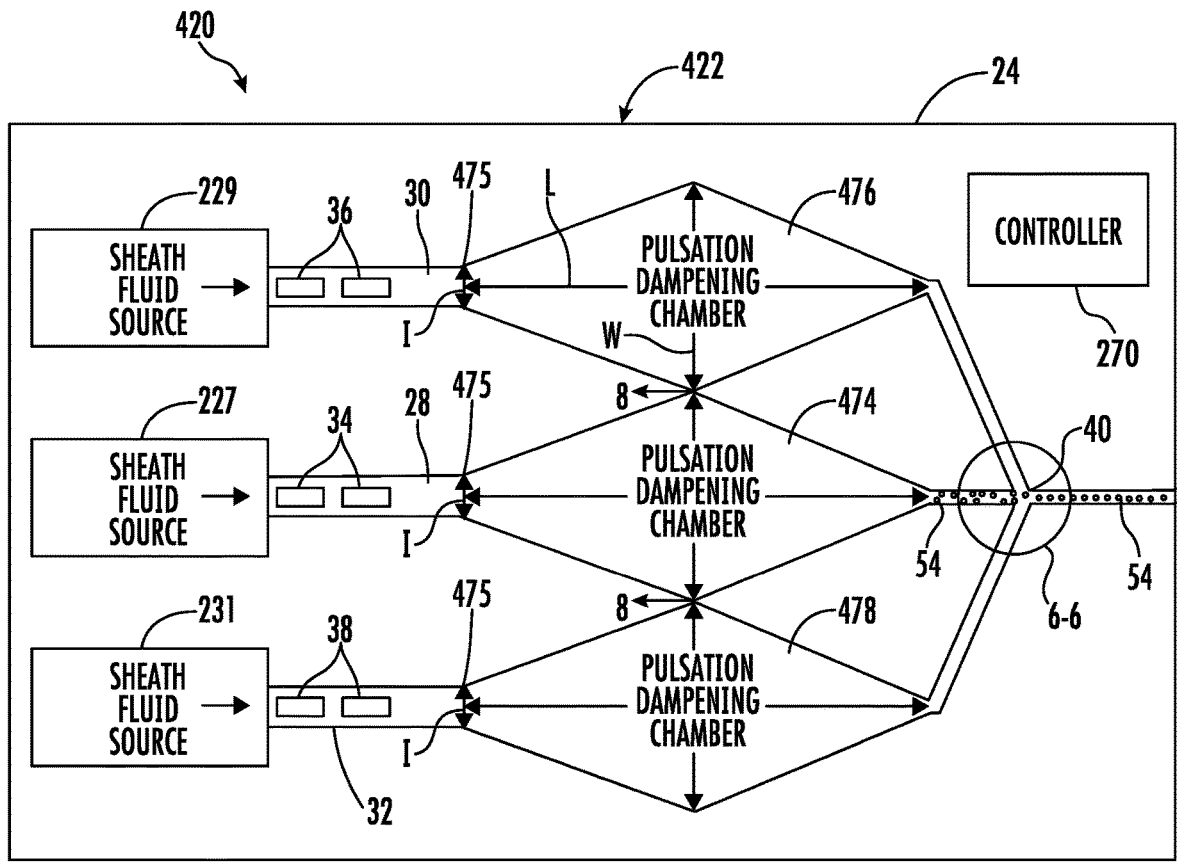
FIG. 5 is a schematic diagram illustrating portions of an example microfluidic device and portions of an example object focuser.

FIG. 5 schematically illustrates portions of another example microfluidic device 420 comprising portions of an example object focuser 422. Object focuser 422 is similar to object focuser 222 except that object focuser 422 utilizes pulsation dampening chambers to reduce the effects of pulses are wave fronts resulting from the use of inertial pumps to enhance object focusing. Object focuser 422 is similar to object focuser 222 except that object focuser 422 additionally comprises pulsation dampening chambers 474, 476 and 478. Those remaining components of object focuser 422 which correspond to object focuser 222 are numbered similarly.

Pulsation dampening chambers 474, 476, 478 comprise chambers along fluid passages 28, 30 and 32, situated between inertial pumps 34, 36 and 38 and convergence 40, respectively. Each pulsation dampening chamber 474, 476 and 478 has a width W larger than the inlet 475 from the portion of the connected fluid passage containing the inertial pump so as to absorb or dissipate forces from the pulses are wave fronts entering the chamber. In one implementation, each of chambers 474, 476 and 478 has an inlet dimension I, a width W at least three times the inlet dimension I and a length L at least three times the inlet dimension I. although each of chambers 474, 476 and 478 are illustrated as being diamond-shaped, in other implementations, the pulsation dampening chambers 474, 476 and 478 may have other shapes, such as round or oval. In other implementations, each of the pulsation dampening chambers 474, 476 and 478 may have other polygonal shapes such as square, rectangular, hexagonal and the like. Although the pulsation dampening chambers 474, 476, 478 are illustrated as being similarly located between inertial pumps 34, 36, 38 and convergence 40, in other implementations, the pulsation dampening chambers 474, 476 and 478 may be positioned differently relative to their respective inertial pumps and convergence 40. Although pulsation dampening chambers 474, 476 and 478 are each illustrated as having a same shape and size, in other implementations, pulsation dampening chambers 474, 476 and 470 may have different sizes and/or shapes relative to one another.

In the example illustrated, each of inertial pump 34, 36 and 38 is illustrated as comprising multiple distinct fluid actuators, wherein the collective group fluid actuators of each inertial pump 34, 36, 38 is asymmetrically positioned between the respective fluid source and the inlet of the respective pulsation dampening chamber 474, 476, 478. As a result, fluid from sources 227, 229 and 231 may be inertially pumped in a direction towards pulsation dampening chambers 474, 476 and 478, respectively, and ultimately across such chambers to convergence 40 where the objects are focused into a single file or near-single file series of objects.

In one implementation, controller 270 may coordinate the activation of the different fluid actuators of each inertial pump 34, 36, 38 to enhance inertial pumping. In one implementation, controller 270 may additionally coordinate the activation of the different inertial pumps 34, 36 and 38 to further reduce the impact of pulses are wave fronts by substantially synchronizing the wave fronts of the different pulses at convergence 40. In other implementations, the wave fronts of the different pulses may be effectively dissipated by chambers 474, 476 and 478 such that controller 270 does not necessarily coordinate the activation of the different inertial pumps 34, 36 and 38 with respect to one another for the purpose of synchronizing wave fronts at convergence 40.

Figure 6:
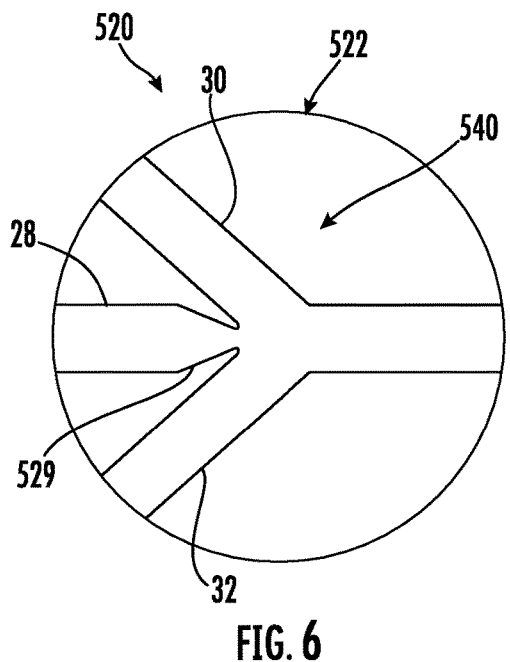
FIG. 6 is an enlarged view illustrating portions of an example microfluidic device and portions of an example object focuser.

FIG. 6 is an enlarged view of a portion of another example microfluidic device 520, taken along line 6-6 of FIG. 5. Microfluidic device 520 comprises object focuser 522 which is similar to object focuser 422 except that object focuser 522 comprises the illustrated convergence 540. As shown by FIG. 6, sample fluid passage 28 comprises a tapering portion or funnel 529 connected to convergence 540. Funnel 529 further assists in focusing objects 54 at convergence 540 and downstream of convergence 540.

Figure 7:
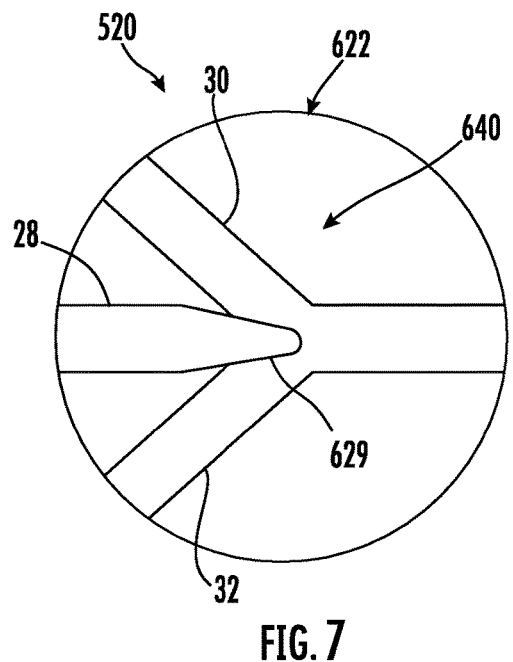
FIG. 7 is an enlarged view illustrating portions of an example microfluidic device and portions of an example object focuser.

FIG. 7 is an enlarged view of a portion of another example microfluidic device 620, taken along line 6-6 of FIG. 5. Microfluidic device 620 comprises object focuser 622 which is similar to object focuser 422 except that object focuser 622 comprises the illustrated convergence 640. As shown by FIG. 7, sample fluid passage 28 comprises a tapering portion or funnel 629 which extends into convergence 540, at least partially passed the entrance of the stream the fluid from sheath fluid passages 30 and 32. Funnel 629 further assists in focusing objects 54 at convergence 640 and downstream of convergence 640.

Figure 8:
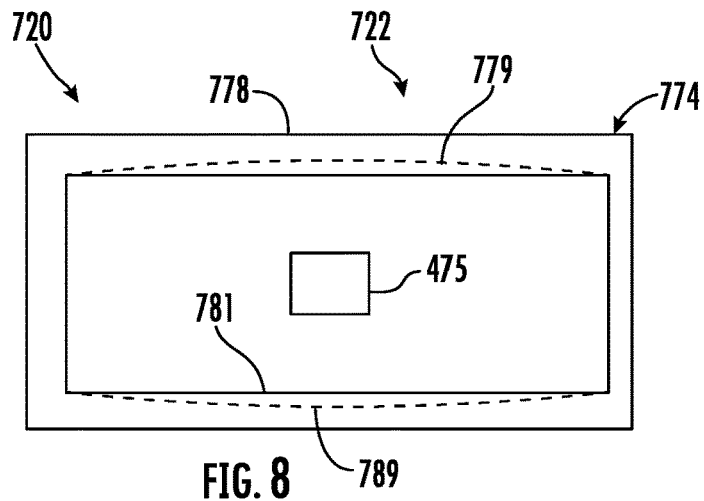
FIG. 8 is a sectional view illustrating portions of an example pulsation dampening chamber of an example object focuser.

FIG. 8 is a sectional view of another example microfluidic device 720 taken along line 8-8 of FIG. 5. Microfluidic device 720 is similar to microfluidic device 420 described above except that microfluidic device 720 comprises object focuser 722. Object focuser 722 is itself similar to object focuser 422 except that object focuser 722 comprises pulsation dampening chamber 774 shown in FIG. 8. In one implementation, the other pulsation dampening chambers, pulsation dampening chambers 476 and 478 shown in FIG. 5 are similar to the pulsation dampening chamber 774 shown in FIG. 8.

In the example illustrated in FIG. 8, pulsation dampening chamber 774 has at least one resiliently compliant inner surface 776 is to change dimensions in response to fluid pressure pulses passing through inlet 475 and produced by the activation the inertial pump 34 (shown in FIG. 5). In one implementation, the resiliently compliant interior surface 776 has sufficient flexibility so as to change from a first dimension to a second larger dimension (shown in broken lines) in response to the fluid pressure pulses, wherein the larger dimension or expansion of the surface 776 result in an increase in the volume of chamber 774 by at least 10 picoliters.

In the example illustrated in FIG. 8, pulsation dampening chamber 774 comprises a wall 778 form from a resiliently compressible material such that surface 776 expands outwardly to the state shown by broken lines 779, compressing wall 778 in response to the fluid pressure pulses. In some implementations, the outer dimensions of pulsation dampening chamber 774 do not change as the wall 778 is compressed. In other implementations, in addition to being compressed, wall 778 may outwardly expand to further increase the volume of pulsation dampening chamber 774 so as to further dissipate the pressure pulses from the inertial pump 34.

Figure 9:
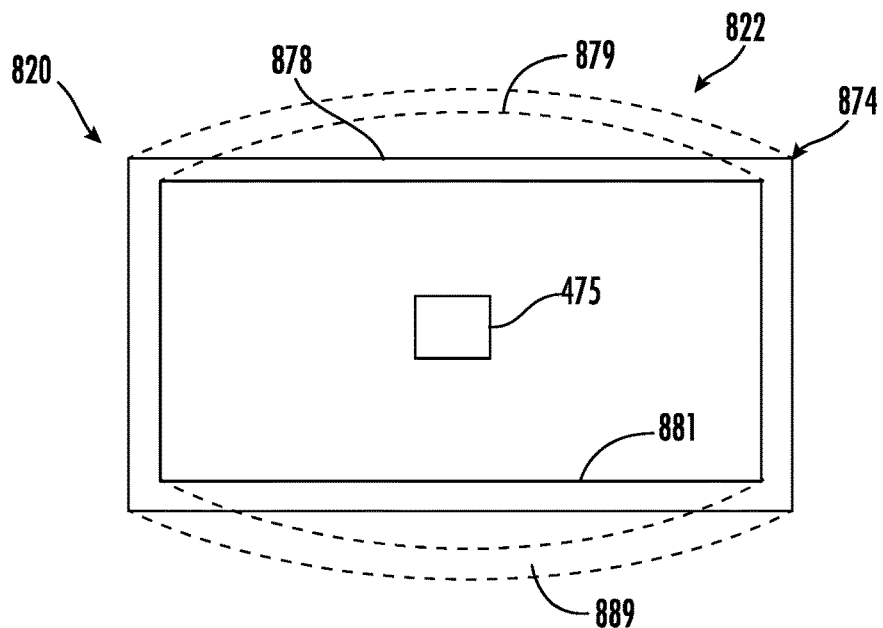
FIG. 9 is a sectional view illustrating portions of an example pulsation dampening chamber of an example object focuser.

FIG. 9 is a sectional view of another example microfluidic device 820 taken along line 8-8 of FIG. 5. Microfluidic device 820 is similar to microfluidic device 420 described above except that microfluidic device 820 comprises object focuser 822. Object focuser 822 is itself similar to object focuser 422 except that object focuser 822 comprises pulsation dampening chamber 874 shown in FIG. 9. In one implementation, the other pulsation dampening chambers, pulsation dampening chambers 476 and 478 shown in FIG. 5 are similar to the pulsation dampening chamber 874 shown in FIG. 9.

As with pulsation dampening chamber 774 described above, pulsation dampening chamber 874 comprises a resiliently compliant interior surface 876 that changes shape or dimension so as to increase the interior volume of chamber 874, dissipating forces from the pulses produced by inertial pump 34 (shown in FIG. 5). In the example shown in FIG. 9, chamber 874 comprises a wall 878 that is sufficiently flexible so as to outwardly bend or flex to the state shown in broken lines 879 so as to increase the interior volume of chamber 874. In one implementation, wall 878 does not compress as it flexes outwardly as shown. In other implementations, wall 878 may additionally be compressed to further increase the increase in the volume of the interior of chamber 874. In one implementation, wall 878 flexes to the state shown in broken lines by sufficient distance so as to increase the volume of chamber 874 by at least 10 picoliters.

Although chambers 774 and 874 are illustrated as having walls 778 and 878 extending along a top of the chambers, such walls may alternatively extend along other portions of such chambers, such as the sides or bottoms of such chambers. Although chambers 774, 874 are illustrated as having a single resiliently compliant interior surface that changes in shape or dimension, in other implementations, each of such chambers 774, 874 may have multiple different resiliently compliant interior surfaces. For example, in one implementation, chamber 8774 may comprise an additional resiliently compliant surface 781, opposite surface 776, which outwardly extends to the state shown by broken lines 789, compressing its wall and further increasing the volume of the dissipation chamber 774. Likewise, chamber 874 may comprise an additional resiliently flexible wall 881, opposite the wall 878, which may flex or stretch to the state shown by lines 889, further increasing the volume of chamber 8742 further dissipate the force from pulses produced by inertial pump 34.

In one implementation, each of the pulsation dampening chambers 474, 476 and 478 shown in FIG. 5 have at least one resiliently compliant interior surface similar to that shown in FIG. 8 or FIG. 9. In such an implementation, each of the pulsation dampening chambers has an interior volume, prior to any movement of the at least one resiliently compliant interior surface, prior to any stretching of the wall or compression of the wall, that is larger than inlet 475. In one implementation, each of the pulsation dampening chambers has an interior volume, prior to any movement of the at least one resiliently compliant interior surface, with a width W and a length L, each of which is at least three times the dimension I of inlet 475. In other implementations, the length L and/or the width W of each of such pulsation dampening chambers may be reduced relative to the dimension I of inlet 475 where the chamber is provided with at least one resiliently compliant interior surface similar to that described above with respect to FIGS. 8 and 9. In some implementations, the "pulsation dampening chamber" may have the same dimensions as that of inlet 475 along its length, having an unstretched uncompressed shape and size similar to that of passage 28, but where the "pulsation dampening chamber" has a changeable interior volume due to the provision of a resiliently compliant interior surface 781 or 881.

Figure 10:
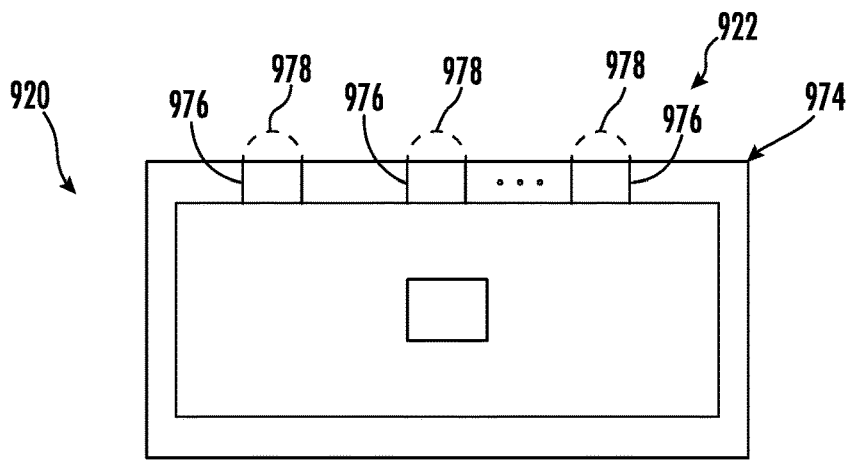
FIG. 10 is a sectional view illustrating portions of an example pulsation dampening chamber of an example object focuser.

FIG. 10 is a sectional view of another example microfluidic device 920 taken along line 8-8 of FIG. 5. Microfluidic device 920 is similar to microfluidic device 420 described above except that microfluidic device 920 comprises object focuser 922. Object focuser 922 is itself similar to object focuser 422 except that object focuser 922 comprises pulsation dampening chamber 974 shown in FIG. 10. In one implementation, the other pulsation dampening chambers, pulsation dampening chambers 476 and 478 shown in FIG. 5 are similar to the pulsation dampening chamber 974 shown in FIG. 10.

Pulsation dampening chamber 974 comprises at least one opening or port 976 forming a fluid meniscus (liquid-gas interface). In the example illustrated, pulsation dampening chamber 974 comprises a plurality of ports 974 above the dampening chamber, wherein the fluid within the chamber forms a meniscus 978 across he said such ports 976 which expands and contracts as the pressure wave enters the chamber to dampen or dissipate the pulsations. In one implementation, the number of ports 976 and their sizes facilitate and increase in the volume of chamber 874 by at least 10 picoliters.

Although the present disclosure has been described with reference to example implementations, workers skilled in the art will recognize that changes may be made in form and detail without departing from the scope of the claimed subject matter. For example, although different example implementations may have been described as including features providing benefits, it is contemplated that the described features may be interchanged with one another or alternatively be combined with one another in the described example implementations or in other alternative implementations. Because the technology of the present disclosure is relatively complex, not all changes in the technology are foreseeable. The present disclosure described with reference to the example implementations and set forth in the following claims is manifestly intended to be as broad as possible. For example, unless specifically otherwise noted, the claims reciting a single particular element also encompass a plurality of such particular elements. The terms "first", "second", "third" and so on in the claims merely distinguish different elements and, unless otherwise stated, are not to be specifically associated with a particular order or particular numbering of elements in the disclosure.

What is claimed is:

1. An object focuser comprising:
a substrate;
a sample fluid passage supported by the substrate;
a first inertial pump supported by the substrate to pump a sample fluid entraining an object through the sample fluid passage;
a first sheath fluid passage;
a second inertial pump supported by the substrate to pump a first sheath fluid through the first sheath fluid passage; and
a second sheath fluid passage;
a first pulsation dampening chamber along the sample fluid passage between the first inertial pump and the convergence;
a second pulsation dampening chamber along the first sheath passage between the second inertial pump and the convergence;
a third pulsation dampening chamber along the second sheath passage between the third inertial pump and the convergence;
a third inertial pump supported by the substrate to pump a second sheath fluid through the second sheath fluid passage, wherein the first sheath fluid passage and the second sheath fluid passage are connected to the sample fluid passage at a convergence on opposite sides of the sample fluid passage.

2. The object focuser of claim 1 further comprising a controller to output control signals such that the wave fronts are synchronized at the convergence.

3. The object focuser of claim 2, wherein each of the first pulsation dampening chamber, the second pulsation dampening chamber and the third pulsation dampening chamber has an inlet, a width at least three times a maximum dimension of the inlet and a length at least three times the maximum dimension of the inlet.

4. The object focuser of claim 3, wherein at least one of the first pulsation dampening chamber, the second pulsation dampening chamber and the third pulsation dampening chamber has at least one resiliently compliant interior surface to change dimensions in response to fluid pressure pulses.

5. The object focuser of claim 1, wherein the fluid sample passage tapers at the convergence.

6. The object focuser of claim 1, wherein each of the first pulsation 2 dampening chamber, the second pulsation dampening chamber and the third 3 pulsation dampening chamber has an inlet, a width at least three times a 25 maximum dimension of the inlet and a length at least three times the maximum dimension of the inlet.

7. The object focuser of claim 1, wherein at least one of the first pulsation dampening chamber, the second pulsation dampening chamber and the third pulsation dampening chamber has at least one resiliently compliant interior surface to change dimensions in response to fluid pressure pulses.

8. The object focuser of claim 7, wherein the at least one of the first pulsation dampening chamber, the second pulsation dampening chamber and the third pulsation dampening chamber comprises a flexible wall providing the at least one resiliently compliant interior surface.

9. The object focuser of claim 7, wherein the at least one resiliently compliant interior surface is to change from a first dimension to a second dimension in response to the fluid pressure pulses, the second dimension increasing a volume of said at least one first pulsation dampening chamber, second pulsation dampening chamber and third pulsation dampening chamber by at least 10 picoliters.

10. The object focuser of claim 1, wherein at least one of the first pulsation dampening chamber, the second pulsation dampening chamber and the third pulsation dampening chamber comprises at least one port forming a gas-liquid interface for forming an expandable meniscus.

11. An object focusing method comprising:
pumping a sample fluid entraining an object through a sample passage on a substrate with a first inertial pump on the substrate;
pumping a first sheath fluid through a first sheath fluid passage on the substrate with a second inertial pump on the substrate, the second sheath fluid passage being connected to the sample passage on a first side of the sample passage at a convergence; and
pumping a second sheath fluid through a second sheath fluid passage on the substrate with a third inertial pump on the substrate, the second sheath fluid passage being connected to the sample passage on a second side of the sample passage at the convergence and
wherein an impact of pulsations or waves is reduced through a first pulsation dampening chamber along the sample passage between the first inertial pump and the convergence, a second pulsation dampening chamber along the first sheath passage between the second inertial pump and the convergence, and a third pulsation dampening chamber along the second sheath passage between the third inertial pump and the convergence.

12. The object focuser of claim 11 further comprising dampening fluid pressure pulsations exhibited at the convergence.

13. A method comprising:
pumping pulses of a sample fluid entraining an object through a sample fluid passage;
pumping pulses of a first sheath fluid through a first sheath fluid passage connected to the sample fluid passage at a convergence;
pumping pulses of a second sheath fluid through a second sheath fluid passage connected to the sample fluid passage at the convergence; and
controlling the pumping of the sample fluid, the pumping of the first sheath fluid and the pumping of the second sheath fluid such that wave fronts of the respective pulses are synchronized at the convergence
wherein an impact of pulsations or waves is reduced through a first pulsation dampening chamber along the sample passage between the first inertial pump and the convergence, a second pulsation dampening chamber along the first sheath passage between the second inertial pump and the convergence, and a third pulsation dampening chamber along the second sheath passage between the third inertial pump and the convergence.

* * * * *